United States Patent [19]

Grau

[11] 4,019,129
[45] Apr. 19, 1977

[54] METALLIC PLATING TESTING APPARATUS

[75] Inventor: Thomas George Grau, Westerville, Ohio

[73] Assignee: Bell Telephone Laboratories, Incorporated, Murray Hill, N.J.

[22] Filed: June 2, 1975

[21] Appl. No.: 582,722

[52] U.S. Cl. .............................. 324/30 R; 204/1 T; 204/195 R; 324/51; 324/52

[51] Int. Cl.$^2$ ................. G01N 27/46; G01N 31/02

[58] Field of Search ........... 204/1 T, 195 R, 195 C; 324/30 R, 51, 52

[56] References Cited

UNITED STATES PATENTS

| | | | |
|---|---|---|---|
| 2,894,882 | 7/1959 | Strodtz | 204/195 R |
| 2,960,455 | 11/1960 | Frankenthal | 204/195 R |
| 2,962,426 | 11/1960 | Sharpsteen | 204/1 T |
| 3,337,440 | 8/1967 | Nestor | 204/195 C |
| 3,356,597 | 12/1967 | Schmidt | 204/195 R |
| 3,494,837 | 2/1970 | Messner et al. | 204/1 T |
| 3,551,801 | 12/1970 | Wood et al. | 204/195 R |
| 3,719,884 | 3/1973 | Laroche | 204/1 T |
| 3,806,800 | 4/1974 | Bove et al. | 324/51 |
| 3,808,105 | 4/1974 | Rozeanu | 204/1 T |

*Primary Examiner*—J. Tung
*Attorney, Agent, or Firm*—William H. Kamstra

[57] ABSTRACT

Apparatus for determining the presence, quantity, size, and location of corrosion causing pores and insulating films on metallic platings is described herein. With the plating acting as an anode, a coordinate array of electrochemical cells is formed by placing an electrolytic film on the plating and sequentially energizing a coordinate array of cathode conductors in the film. A digital voltmeter is connected to the plating anode and registers varying potentials as the cathode conductors are energized depending upon the presence, etc., of pores in and films on the plating. Information derived from the voltmeter output controls a printer, in one embodiment, to record the sequential output information. Correlation of the recorded information with the sequence in which the cathode conductors are energized indicates the location of the undesirable plating surface conditions.

12 Claims, 1 Drawing Figure

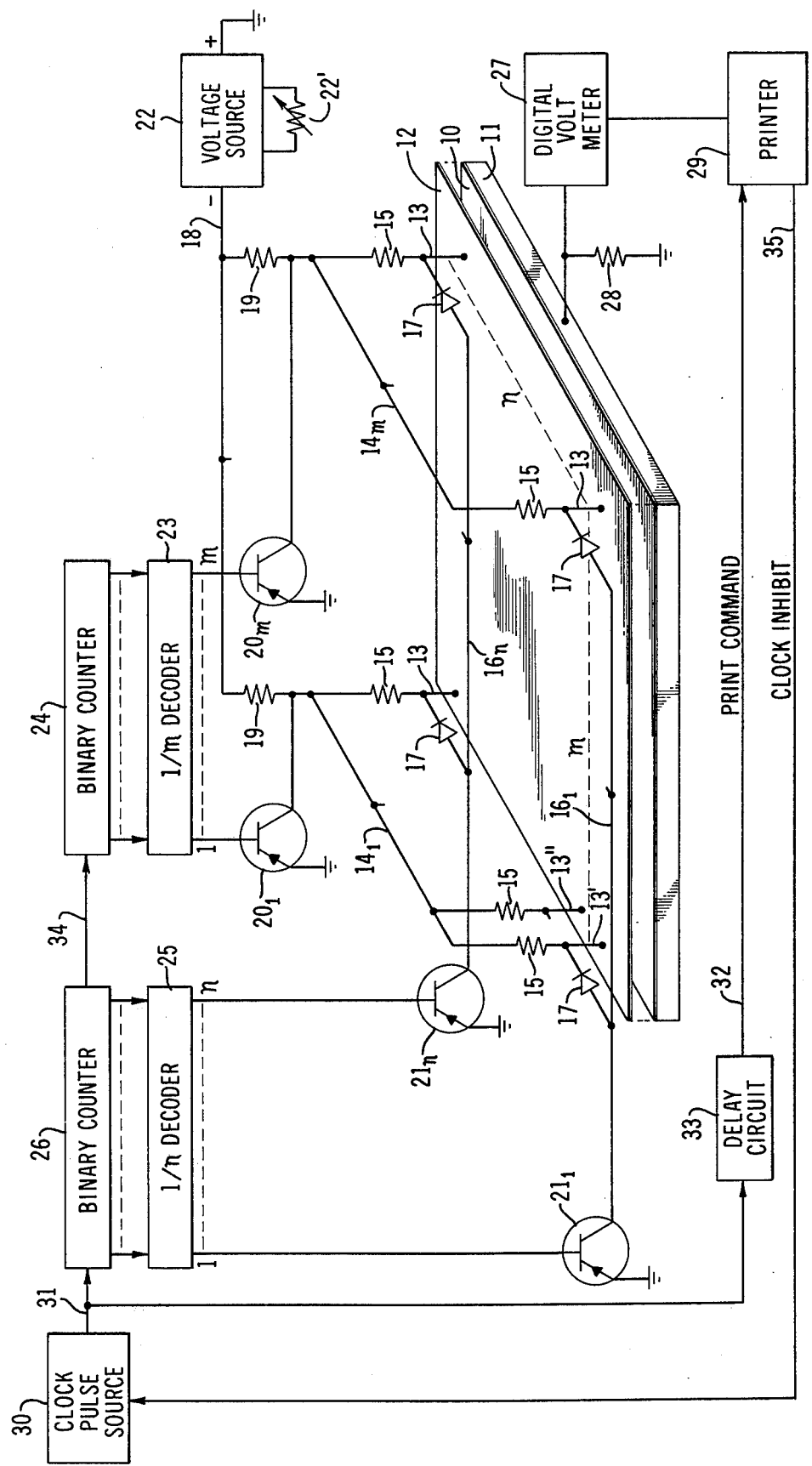

METALLIC PLATING TESTING APPARATUS

BACKGROUND OF THE INVENTION

This invention relates to testing and measuring apparatus and more particularly to such apparatus for inspecting metallic plating on electrical interconnections. The invention in an exemplary use is advantageously applicable to the testing of interconnection surfaces of printed wiring boards and it is in this context that an illustrative embodiment of the invention will be described.

As is known, printed wiring boards, in addition to having a pattern of electrical conductors formed thereon, also are provided with printed conductor interconnection fingers. These fingers are arranged on a wiring board in a manner to provide electrical continuity between the conductor pattern and external circuitry when inserted into a specific connector means. In order to ensure a reliable electrical contact with the connector means for the life of the wiring board, a thin gold plating is added to the metallic contacting surface of the fingers. The necessary reliability is achieved, however, only if the gold plating itself presents an even, uncontaminated and continuous surface. Although gold is not vulnerable to the formation of oxides or tarnish films, these products may originate from the substrate metal when pores in the plating expose the underlying metal surface. These corrosion products are frequently able to insulate a contact surface to a degree which renders a reliable electrical contact impossible. It accordingly becomes necessary in the fabrication of printed wiring board interconnections and in other metallic plating applications to examine for, and to locate, any pores in the surface of a plating which extend to the underlying substrate and for films on the surface. In the past, the plated surface, by one method, was visually examined for porosity by superimposing an electrolytic blotter on the surface, discoloration at the pore points then revealing their presence. This method obviously has the shortcoming of being largely subjective with considerable possibility for error. Other visual methods are open to the same possibilities for mistake.

It is, accordingly, one object of this invention to provide apparatus for ensuring the detection of pores in a metallic plating. Another object is to provide such apparatus which will also generate data regarding the number, size, and location of the pores detected.

A further object of this invention is to provide apparatus which in addition to detecting pores in a metallic plating, will advantageously also detect the presence of nonconductive surface films on such plating.

SUMMARY OF THE INVENTION

The foregoing and other objects of this invention are realized in one illustrative embodiment thereof in which a coordinate array of electrochemical cells are formed in association with the metallic plating by placing an electrolytic film on the plating and arranging a coordinate array of cathode elements in the film, the substrate on which the plating is deposited acting as an anode. The single anode is connected to a digital voltmeter and each cathode element is connected to a distributor through which a power source applies predetermined potentials sequentially to the cathodes of the array. Values of the currents appearing in the cathodes are detected and from these values and the identification of the cathodes, the number, size, and location of corrosion producing pores are determined. A moist filter paper advantageously holds the electrolyte, which in one embodiment consisted of a weak solution of sulphuric acid and copper sulfate.

At each of the electrolytic cells of the array, the response to an applied voltage permits current measurements which are indicative of the character of the pores detected (and that of insulating films). By limiting the voltage to a predetermined level, conduction of current through the electrolyte from a cathode element will be to the anode only at pore sites where dissolution of the substrate metal occurs. No reaction takes place at gold plated areas of the anode material when the magnitude of the cathode to anode voltage is less than some critical value. This characteristic together with the fact that the voltage drop from the cathode element to the pore site increases as the conducting path distance increases makes possible the location of a pore site. Conducting path length is a factor because of the conductivity of the electrolyte and the resistivity of the filter paper medium. As the applied voltage level increases, reactions in the electrolyte at the anode plating take place. These reactions increase the current between a cathode element and plating surface nearest the element. In the absence of porosity in the plating, substantially the same current is present at each cathode in the coordinate array. When ports are present in the plating, the magnitude of the current may be thought of as the sum of the current to the pore sites and the current to the plated surface. When an insulating film is present, the path from certain of the cathode elements is increased and the current is correspondingly reduced which permits the detection of the films.

The current value representative output of the digital voltmeter is employed, in one illustrative embodiment of the invention, to control a printing means for generating a listing of numerical information regarding the presence (or absence) of pores and insulating films on the plating being tested. By correlating the sequence of information items in the listing with the sequence in which the cathodes are energized, the specific areas being tested may be determined.

A feature of a test apparatus according to this invention is thus the formation of an electrochemical cell between a test cathode and the substrate of a plating under test, the magnitude of the current in the cell being indicative of the condition of the plating in the near vicinity of the test cathode.

Another feature of a test apparatus according to this invention is a coordinate array of the aforementioned electrochemical cells in association with a plated surface for systematically examining the condition of the plated surface and for loading specific conditions on the surface.

BRIEF DESCRIPTION OF THE DRAWING

The foregoing and other objects and features of a test apparatus according to the principles of this invention will be better understood from a consideration of the detailed description of the organization and operation of one specific illustrative embodiment thereof which follows when taken in conjunction with the accompanying drawing in which the single FIGURE depicts largely in block symbol form and in enlarged scale for the sake of clarity an illustrative plating test appartus according to this invention, the plating area being shown in three-dimensional, perspective view.

DETAILED DESCRIPTION

One illustrative testing arrangement according to this invention is shown in the drawing in association with a plating 10 to be examined for the presence of pores and insulating films. The plating 10, which may be gold, is formed on a substrate 11, which normally comprises a conductive metal such as copper. Superimposed on the plating 10 is a paper sheet 12 sufficiently absorbent to hold an electrolytic liquid to be more specifically considered hereinafter. Although the sheet 12 is shown separated from the plating 10 in order to note the separate elements, in practice the sheet 12 is in physical contact with plating 10. A plurality of conductors 13, only representative ones of which are shown, in electrical contact with the electrolyte of the sheet 12, are arranged in an mn coordinate array. The conductors 13 viewed in their arrangement along the $n$ coordinate rows are connected together by rows at their ends to respective common row buses $14_1$ through $14_m$ through individual conductor resistors 15. The same conductors 13 viewed in their arrangement along the $m$ coordinate columns are connected together by columns at their ends to respective common column buses $16_1$ through $16_n$ through individual diodes 17.

Each of the row buses 14 is connected to a common power bus 18 through an individual resistor 19. The buses 14 are also individually connected to the collectors of respective PNP transistors 20. The emitters of transistors 20 are connected to ground. The $m$ coordinate buses 16 are connected to the collectors of respective PNP transistors 21, the emitters of which are also connected to ground. Only representative ones of the transistors 20 and 21 are shown in the drawing. The power bus 18 is connected to the negative output of a power source 22, the character of which will be more specifically considered hereinafter. Each of the bases of transistors 20 is connected to a corresponding output of a 1-out-of-$m$ decoder circuit 23 which in turn is connected by its inputs to corresponding outputs of a binary counter 24. The bases of transistors 21 are connected to corresponding outputs of a 1-out-of-$n$ decoder 25 which in turn is connected by its inputs to corresponding outputs of a binary counter 26. Turning to the circuitry extending in the opposite direction from the plating 10, the latter is electrically connected to a digital voltmeter 27 and to ground via a resistor 28; the voltmeter 27 has its output connected to a printer 29. Each of the circuits generally referred to in the foregoing is under the timing control of a clock pulse source 30, the binary counter 26 directly via a conductor 31 and the printer 29 via a print command conductor 32 and a delay circuit 33. Binary counter 24 is controlled by over-flow clock pulses from counter 26 via a conductor 34 as will be more fully described hereinafter. Finally, clock pulse source 30 itself may be controlled by a signals originating at printer 29 via a clock inhibit conductor 35.

The circuitry directly associated with the plating 10 to be examined as actually practiced in one illustrative embodiment of the invention may now be more specifically considered. In the electrochemical arrangement contemplated, the conductors 13 function as cathodes, or as will be seen, more accurately a multi-element cathode, the plating 10 itself acting as an anode. The electrolyte termination of the conductors 13 present in practice a planar surface whose dimensions are determined by the dimensions of the printed wiring board plated surface to be examined — in one case, 0.10 inches by 0.15 inches. The dimensions of, and the spacings between, the conductors 13 are similarly determined by the size and spacings anticipated for possible pores in the plating 10. In the same case just referred to, the conductors 13 were square in cross-section, being 0.0028 inches on a side, and positioned to an ultimate spacing of 0.005 inches on centers. The electrolyte for one illustrative testing apparatus was chosen in view of factors such as its conductivity, the reactions to be expected at the plating surface, and the like. Thus, one electrolyte which proved suitable in practice was a concentration of sulphuric acid and copper sulfate, being approximately 0.01 and 0.0001 gram equivalents, respectively. The details of the circuits and apparatus shown in the drawing in block symbol form will be readily envisioned by one skilled in the art when described in terms of their operation in the following; accordingly, a detailed description of their included circuit elements is not necessary for a complete understanding of this invention. With the foregoing description of the organization of one specific testing arrangement according to this invention in mind, a typical testing operation thereof may now be considered.

Once the electrochemical cells of the coordinate array at the coordinates located by the conductors 13 have been formed on the plating 10, the peripheral circuitry is controlled to sequentially connect the conductors 13 to voltage source 22 and to measure the current through each as it appears therein. When the printer 29, which may suitably comprise a teletypewriter, has been prepared for operation, the latter terminates a clock inhibit signal which has been maintaining the clock pulse source 30 in its "OFF" state via clock inhibit conductor 35. As a result, source 30 begins to generate periodic pulses which are applied to the input of binary counter 26. As the latter circuit is stepped along, output signals sequentially appear on its output which signals are in turn sequentially applied to the inputs of decoder circuit 25. The latter circuit decodes the binary inputs thus applied to decimal outputs to in turn sequentially apply control pulses to transistors 21. The latter transistors as well as transistors 20 are normally conductive to complete current paths from ground to the negative output of source 22. Thus, for example, normally conductive transistor $21_1$ connects ground at its emitter to the common bus $16_1$ via its collector, the current path extending via diodes 17, resistors 15 and 19, common conductor 18 to the negative output of source 22. Current paths are similarly traceable under the control of the remaining normally conductive transistors 21 of the sequence terminating in transistor $21_n$. As mentioned in the foregoing, similar circuit paths are provided by the normally conductive transistors 20. Thus, for example, transistor $20_1$ connects ground at its emitter to the common conductor 18 via its collector and resistor 19. Current paths are similarly traceable under the control of the remaining normally conductive transistors 20 of the sequence terminating in transistor $20_m$.

As the first output of decoder 25 is selected responsive to a decoded input from counter 26, a positive signal is applied to the base of transistor $21_1$ to render this transistor nonconductive and open one path to ground therethrough from the common bus $16_1$. After $n$ clock pulses, an over-flow pulse from counter 26 is applied to the input of counter 24 via conductor 34. (No cathode currents flow during the first $n$ clock pulses since transistors 20 provide current paths for all of the buses 14.) Counter 24 is stepped one position representative of a binary value which is decoded to a decimal output position of decoder 23 to apply, as a result, a positive signal at its number one output and hence to the base of transistor $20_1$. The latter transistor is rendered nonconductive thereby opening a path to ground at its emitter for the common conductor 18. At this point, transistor $20_1$ and $21_1$ are turned off with the result that the common power conductor 18 is denied a path to ground through both transistor $20_1$ and the common bus $16_1$. At the array crosspoint location defined by the common conductors $14_1$ and $16_1$, only one path to ground then remains for voltage source 22 and that is through the cathode conductor 13', the electrolytic sheet 12, plating 10, substrate 11, and resistor 28. At each of the remaining crosspoint locations of the array, paths to ground are available, via a bus 14 and a bus 16.

The sequential connection of the cathode conductors 13 with the power source 22 is continued in the manner similar to that described in the foregoing. Thus, as the next succeeding output of decoder 25 has a positive signal applied thereon in response to the control of binary counter 26 and clock pulse source 30, the first transistor $21_1$ is restored to its conductive state and a path to ground is again available for common bus $16_1$. The next succeeding bus 16 is, however, disconnected from ground by the turning off of its associated transistor 21. As binary counter 26 applied its next output the next succeeding decoder 25 input, no over-flow pulse was applied to the input of binary counter 24 via conductor 34. Accordingly, transistor $20_1$ remains turned off with the result that at the crosspoint location defined by the next succeeding common bus 16 and the common bus $14_1$, only one path to ground remains for source 22 and that is now through the cathode conductor 13'', the electrolytic sheet 12, plating 10, substrate 11, and resistor 28. At each of the remaining crosspoint locations of the array, paths to ground are available through a bus 16 and/or bus 14. This sequential process continues through the last cathode conductor 13 defined by the common bus $14_1$ as controlled by the last output of binary counter 26. Up to this point, no further inputs have been received by binary counter 24 with the result that only transistor $20_1$ has been turned off. When counter 26 begins another cycle of operation a second over-flow pulse is transmitted via conductor 34 to binary counter 24 to advance this circuit one step to turn off, under the control of decoder 23, the next succeeding transistor 20 and to restore transistor $20_1$ to its conductive state. The process is continued with counter 24 being advanced one step for each complete cycle of counter 26 until the last cathode conductor 13 at the crosspoint location defined by common bus $14_m$ and common bus $16_n$ has been energized. At each energization of a cathode conductor 13 under the ultimate control of clock pulse source 30, the latter at the same time transmits its periodic output pulse as a print command to printer 29 to begin its recording of the output of digital voltmeter 27. This command pulse is suitably delayed by delay circuit 33 to permit stabilization of the circuit elements for each cathode energization. The character of the inputs to digital voltmeter 27 and their significance in the readout of the apparatus of this invention may now be considered.

As a cathode conductor 13 is energized in the manner described in detail in the foregoing and is made negative with respect to the plating 10 anode, a current will result in resistor 28 from ground to voltage source 22 along a path previously traced. The voltage across resistor 28 is a measure of the current in the conductor 13, being energized, and this voltage appears as digital data on the output of digital voltmeter 27. The manner in which voltage values across resistor 28 are caused to vary as the result of particular surface conditions of the plating 10 is more specifically described as follows.

Assume first the operation of the apparatus according to this invention in testing a plating 10 for porosity. In the practice of this invention it has been demonstrated that, at an applied negative voltage more positive than a predetermined negative voltage — in one case, $-0.7$ volts — but still less than zero volts, as controlled by control 22' of source 22, substantially no current is conducted between a cathode 13 and plating 10 when no pores are present in the plating. This follows from the fact that no chemical reactions were found possible in the electrolyte employed at voltages between zero and $-0.7$ volts. At areas of the plating 10, however, where pores are present, the underlying copper substrate is exposed and chemical reactions in the electrolyte occur with a resulting current being conducted between a cathode 13 and the substrate 11.

Assume, for example, the presence of a pore in plating 10 beneath a given cathode 13. A current $i_1$ is conducted as a result between that cathode 13 and substrate 11. When the next succeeding cathode 13 is energized with same fixed voltage from the source 22 and assuming no porosity beneath the latter cathode, then a second current $i_2$ is conducted from the latter cathode to the substrate 11 due to the chemical reactions at the first pore site. However, since the electrolyte is a resistive medium, the longer the distance from a pore site to an energized cathode, the lower the current magnitude in that path; current $i_1$, as a result, will thus be greater than current $i_2$, for example. As succeeding cathodes 13 are energized, the distances from cathodes 13 to the original pore site become longer and hence the current values in the paths through the electrolyte decrease. Obviously, the presence of additional pores in the vicinity of an energized cathode 13 will increase the current value. However, importantly, the current value will always be a maximum in a cathode 13 nearest to a pore site on the plating 10. If no pores exist in the placing, approximately equal although very small currents appear at each cathode and hence in the resistor 28. Thus, the identification of such a cathode and the detection of the maximum current value provide not only information regarding the presence of a pore, but also its location in the plating.

To recapitulate, two characteristics of the apparatus according to this invention advantageously make possible the porosity testing and location operation: the fact that at a voltage applied to a cathode 13 more positive than a predetermined negative voltage, but less than zero volts, substantially no current is conducted between a cathode 13 and plating 10 when no pores are present and the fact that the resistance of the electrolyte from a cathode 13 to a pore site increases as the path distance increases.

The detection and location of insulating films on the plating are based on the fact that at a voltage applied to a cathode 13 more negative than the aforementioned predetermined negative voltage, reactions between the electrolyte and the metallic plating 10 itself take place. A current is generated as a result, which current is a maximum when the path from a cathode 13 to the plating 10 is unimpeded. Accordingly, in order to detect an insulating film or films, voltage source 22 is controlled by control 22' to provide the second, more negative voltage sequentially to the cathodes 13 in the manner described in the foregoing in a second cycle of operation. When an insulating film is present on the plating 10 at an energized cathode 13, the shortest conducting path through the electrolyte to the surface of the plating 10 is increased and the current magnitude in the path as well as through resistor 28 is reduced.

The current magnitudes at successive energizations of the cathode elements 13 during both cycles of operation, and hence the voltages across resistor 28, are measured by voltmeter 27 which provides a corresponding digital readout indicative of the voltage magnitude input. This digital readout is recorded by printer 29 under control of clock pulses from clock pulse source 30 in a listing covering the entire cycle of cathode energization. By comparing the sequence of the latter energization with the current values listed, the precise location of pore sites and films is readily determined.

What has been described is considered to be only one illustrative testing apparatus according to the principles of this invention and it is to be understood that various and numerous other arrangements may be devised by one skilled in the art without departing from the spirit and scope of the invention as defined by the accompanying claims.

What is claimed is:

1. Apparatus for testing the surface conditions of a metallic plating comprising an electrolytic medium in electrical contact with said plating, an array of cathode elements in electrical contact with said medium, means for applying a test potential individually to said cathode elements in a predetermined sequence, means electrically connected to said plating for measuring currents generated in said medium by said potential between said cathode elements and said plating and for generating output data representative of the magnitude of said currents, and presentation means controlled responsive to said data for presenting said data in a sequence corresponding to said predetermined sequence.

2. Apparatus as claimed in claim 1 in which said medium comprises an absorbent sheet soaked in an electrolyte.

3. Apparatus as claimed in claim 1 in which said presentation means comprises printing means for recording said data.

4. Apparatus as claimed in claim 1 in which said metallic plating comprises an electrical connector surface on a printed wiring board.

5. Apparatus for testing the surface conditions of a metallic plating comprising an absorbent sheet containing an electrolytic solution in physical contact with said plating, an array of electrochemical cells comprising a corresponding array of conductors in electrical contact with said electrolytic solution, said metallic plating, and localized areas of said sheet defined by said array of conductors; means including a power source for applying test potentials individually to said array of conductors in a predetermined sequence, said potentials generating currents in said cells defined by said individual conductors of magnitudes as determined by the said surface conditions at said localized areas; means electrically connected to said plating for measuring said currents and for generating data indicative of the magnitudes of said currents, and presentation means operated responsive to said data for recording said current magnitudes in a sequence corresponding to said predetermined sequence.

6. Apparatus as claimed in claim 5 in which said presentation means comprises teletypewriter means for printing a listing of said current magnitudes.

7. Apparatus for testing the surface conditions of a metallic plating comprising an electrolytic medium in physical contact with said plating, an array of electrochemical cells comprising a corresponding array of conductors in electrical contact with said medium, said metallic plating, and localized areas of said medium defined by said array of conductors; logic means including a power source for applying first predetermined test potentials individually to said conductors in a predetermined sequence, said potentials generating currents in said cells of magnitudes as determined by the presence or absence of pores in said plating at said localized areas; means electrically connected to said plating for measuring said current magnitudes and for generating data signals indicative of said magnitudes, and presentation means operated responsive to said signals for presenting recordings of said current magnitudes in a sequence corresponding to said predetermined sequence.

8. Apparatus as claimed in claim 7, said power source also applying second predetermined test potentials individually to said conductors in said predetermined sequence, said last-mentioned potentials generating currents in said cells of magnitudes as determined by the presence or absence of insulating films on said plating at said localized areas.

9. Apparatus as claimed in claim 8 in which said medium comprises an absorbent sheet saturated with an electrolyte.

10. Apparatus as claimed in claim 9 in which said presentation means comprises a printer means for printing a listing of said current magnitudes.

11. Apparatus as claimed in claim 10 also comprising clock means for controlling the operations of said logic means and said printer means in said predetermined sequence.

12. Apparatus as claimed in claim 11 in which said array of conductors comprises a mn coordinate array.

* * * * *